(12) United States Patent
Yamada et al.

(10) Patent No.: US 6,818,764 B2
(45) Date of Patent: Nov. 16, 2004

(54) PROCESS FOR PREPARING SUBSTANCE GM-95

(75) Inventors: Shozo Yamada, Hanno (JP); Kazuhiko Shigeno, Iruma (JP); Kazuhiro Kitagawa, Hanno (JP); Shigeo Okajima, Tokorozawa (JP); Tetsuji Asao, Kokubunji (JP)

(73) Assignees: Taiho Pharmaceutical Co., Ltd., Tokyo (JP); Sosei Co., Ltd., Tokyo (JP)

( * ) Notice: Subject to any disclaimer, the term of this patent is extended or adjusted under 35 U.S.C. 154(b) by 0 days.

(21) Appl. No.: 10/433,500

(22) PCT Filed: Dec. 12, 2001

(86) PCT No.: PCT/JP01/10870

§ 371 (c)(1),
(2), (4) Date: Jun. 3, 2003

(87) PCT Pub. No.: WO02/48153

PCT Pub. Date: Jun. 20, 2002

(65) Prior Publication Data

US 2004/0049029 A1 Mar. 11, 2004

(30) Foreign Application Priority Data

Dec. 12, 2000 (JP) .......................... 2000-377167

(51) Int. Cl.[7] .................... C07D 513/22; C07D 498/22; C07D 263/34
(52) U.S. Cl. ........................ 540/460; 540/472
(58) Field of Search ................. 540/460, 472

(56) References Cited

FOREIGN PATENT DOCUMENTS

WO  WO-00/24747 A1  5/2000

OTHER PUBLICATIONS

Chattopadhyay, Shitak K. et al. "Towards a total synthesis of ulapualide A. Concise synthetic routes to the tris–oxazole ring system and tris–oxazole macrolide core in ulapualides, kabiramides, halichondramides, mycalolides and halishgamides" J. Chem. Soc., Perkin Trans. 1, Jun. 21, 2000, No. 15, p. 2415–2428.

*Primary Examiner*—Bruck Kifle
(74) *Attorney, Agent, or Firm*—Rader, Fishman & Grauer PLLC

(57) ABSTRACT

A method of manufacturing substance GM-95 having general formula [I], comprising (a) deprotecting a macrocyclic compound having general formula [II] (wherein, $R^1$'s are the same or different and each represents a lower alkyl group, and $R^2$ represents a thiol protecting group) by removing acetal protecting groups (the $R^1$'s) thereof, and forming an oxazole ring through an intramolecular cyclization reaction between produced formyl group and an amide group, and (b) deprotecting a resulting macrocyclic compound having general formula [III] (wherein, $R^2$ is as mentioned above) by removing the thiol protecting group ($R^2$) thereof, and forming a thiazoline ring through an intramolecular cyclization reaction between a thiol group thus produced and an amide group.

6 Claims, 3 Drawing Sheets

PROCESS FOR PREPARING SUBSTANCE GM-95

TECHNICAL FIELD

The present invention relates to a method of manufacturing substance GM-95, which has an anti-cancer activity, and also relates to intermediates in the manufacture of substance GM-95.

BACKGROUND ART

Regarding substance GM-95, which has an anti-cancer activity, International Publication No. WO00/24747 discloses isolation from a culture. The structure of substance GM-95 is unique; it is a macrocyclic compound comprising seven oxazole rings and a thiazoline ring connected together. No chemical manufacturing method has been known for these macrocyclic compounds comprising sequential 5-membered hetero-cyclic rings, such as substance GM-95 so far.

DISCLOSURE OF THE INVENTION

It is an object of the present invention to provide a method of manufacturing substance GM-95, and intermediates in the manufacture of substance GM-95.

That is, the present invention relates to a method of manufacturing substance GM-95 having general formula [I]

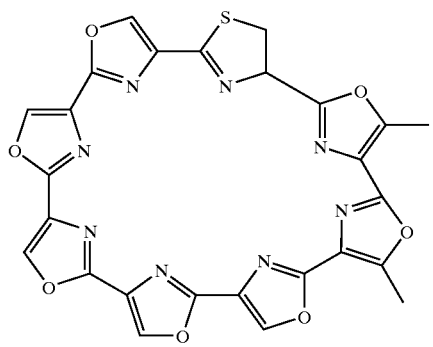

[I]

characterized by (a) deprotecting a macrocyclic compound having general formula [II]

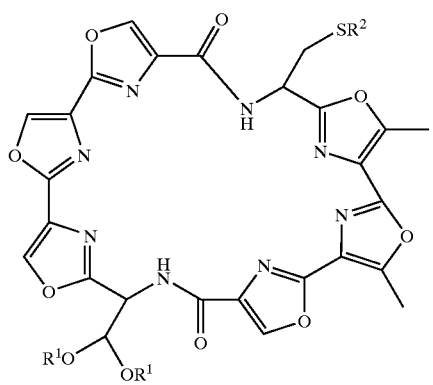

[II]

(wherein, $R^1$'s are the same or different and each represents a lower alkyl group, and $R^2$ represents a thiol protecting group) by removing acetal protecting groups (the $R^1$'s) thereof, and forming an oxazole ring through an intramolecular cyclization reaction between the thus produced formyl group and an amide group, and (b) deprotecting the resulting macrocyclic compound represented by general formula [III]

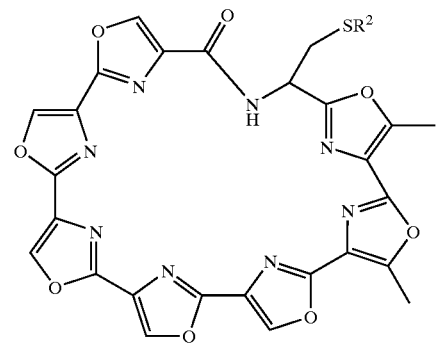

[III]

(wherein, $R^2$ is as mentioned above) by removing the thiol protecting group ($R^2$) thereof, and forming a thiazoline ring through an intramolecular cyclization reaction between a thiol group thus produced and an amide group. Moreover, the present invention relates to the macrocyclic compounds represented by above-mentioned general formulae [II] and [III], which are useful as intermediates in the manufacture of substance GM-95.

Specifically, the present specification provides the following inventions.

Item 1: A method of manufacturing substance GM-95 having general formula [I], characterized by deprotecting the thiol protecting group ($R^2$) of the macrocyclic compound having general formula [III] and forming a thiazoline ring through an intramolecular cyclization reaction between a thiol group thus produced and an amide group.

Item 2: A method of manufacturing substance GM-95 having general formula [I], characterized by (a) deprotecting acetal protecting groups (the $R^1$'s) of the macrocyclic compound having general formula [II] and forming an oxazole ring through an intramolecular cyclization reaction between a formyl group thus produced and an amide group, and (b) deprotecting the thiol protecting group ($R^2$) of the resulting macrocyclic compound having general formula [III] and forming a thiazoline ring through an intramolecular cyclization reaction between a thiol group thus produced and an amide group.

Item 3: The macrocyclic compound having general formula [II].

Item 4: The macrocyclic compound having general formula [III].

Item 5: A method of manufacturing the macrocyclic compound having general formula [II], characterized by (a) carrying out dehydration condensation between an acetal derivative having general formula [IV-a]

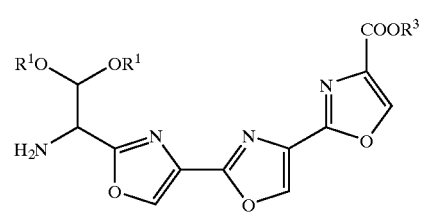

[IV-a]

(wherein, the $R^1$'s are as mentioned above, and $R^3$ represents a carboxyl protecting group) and a thiol derivative having general formula [V-a]

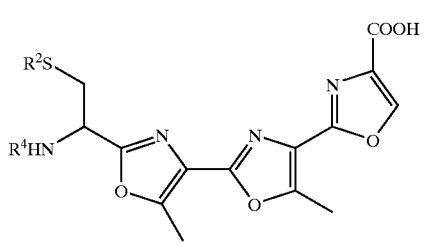

(wherein, $R^2$ is as mentioned above, and $R^4$ represents an amino protecting group), and (b) deprotecting the amino protecting group ($R^4$) and the carboxyl protecting group ($R^3$) of the resulting amide derivative having general formula [VI]

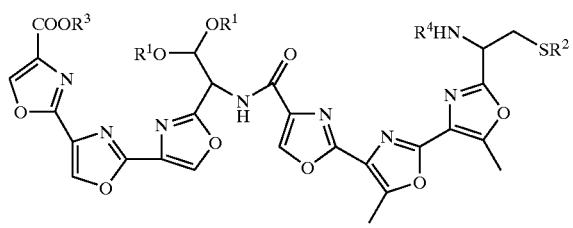

(wherein, the $R^1$'s, $R^2$, $R^3$ and $R^4$ are as mentioned above) and then carrying out intramolecular cyclization.

Item 6: A method of manufacturing the macrocyclic compound having general formula [II], characterized by (a) carrying out dehydration condensation between an acetal derivative having general formula [IV-b]

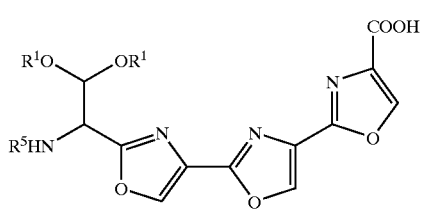

(wherein, the $R^1$'s are as mentioned above, and $R^5$ represents an amino protecting group) and a thiol derivative having general formula [V-b]

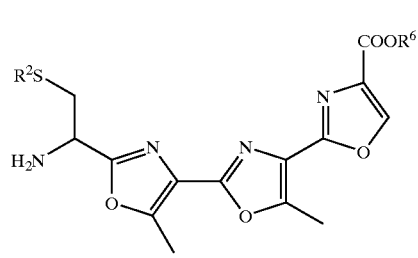

(wherein, $R^2$ is as mentioned above, and $R^6$ represents a carboxyl protecting group), and (b) deprotecting the amino protecting group ($R^5$) and the carboxyl protecting group ($R^6$) of the resulting amide derivative having general formula [VII]

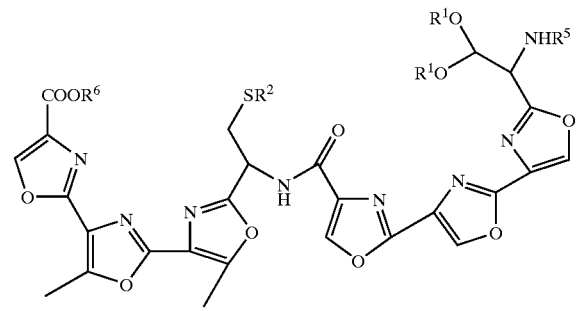

(wherein, the $R^1$'s, $R^2$, $R^5$ and $R^6$ are as mentioned above) and then carrying out intramolecular cyclization.

The scheme of the method of manufacturing GM-95 according to the present invention is shown below.

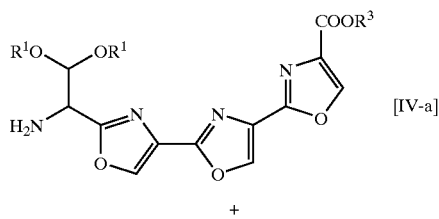

+

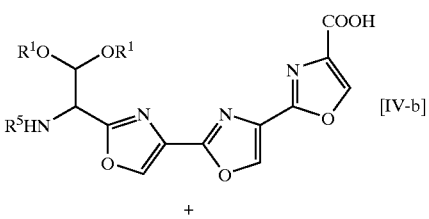

+

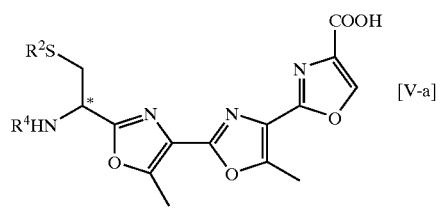 [V-a]

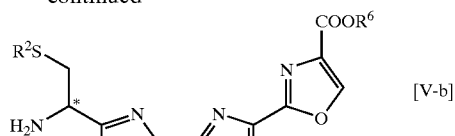 [V-b]

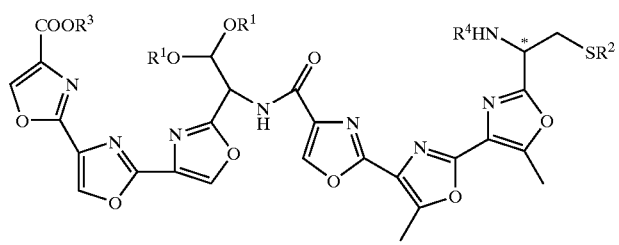 [VI]

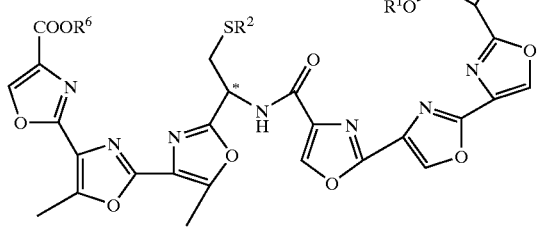 [VII]

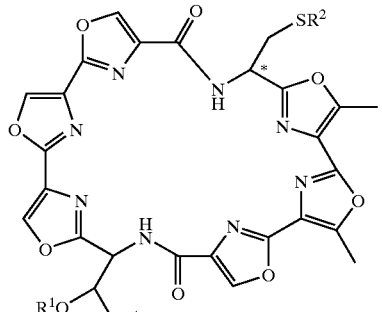 [II]

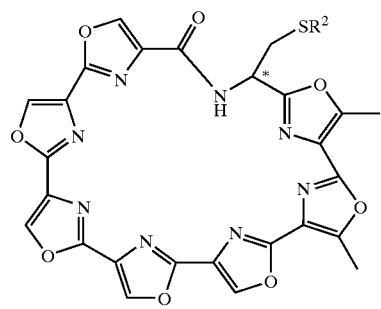 [III]

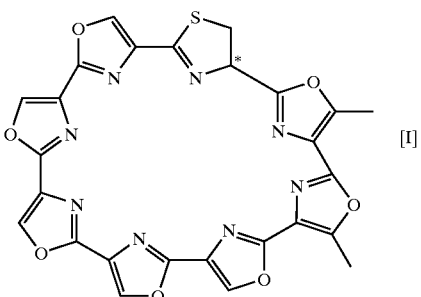 [I]

In the present invention, examples of the lower alkyl groups represented by the $R^1$'s are straight-chain or branched lower alkyl groups having 1 to 6 carbon atoms such as a methyl group, an ethyl group, an n-propyl group, an isopropyl group, an n-butyl group, an isobutyl group, a t-butyl group, and an s-butyl group, with a methyl group or an ethyl group being preferable, and a methyl group being more preferable.

Examples of the thiol protecting group represented by $R^2$ are protecting groups mentioned in 'Protective Groups in Organic Synthesis' (published 1981) by Greene, for example unsubstituted or substituted benzyl groups such as a benzyl group, a p-methoxybenzyl group, a 4-methylbenzyl group, a 3,4-dimethylbenzyl group, a p-hydroxybenzyl group, a p-acetoxybenzyl group and a p-nitrobenzyl group, a diphenylmethyl group, a trityl group, a t-butyl group, an acetyl group, a benzoyl group, and so on, with an unsubstituted or substituted benzyl group such as a benzyl group, a p-methoxybenzyl group, a 4-methylbenzyl group, a 3,4-dimethylbenzyl group, a p-hydroxybenzyl group, a p-acetoxybenzyl group or a p-nitrobenzyl group, or a diphenylmethyl group, a trityl group, or a t-butyl group being preferable, and a benzyl group, a trityl group, or a t-butyl group being more preferable.

In the present invention, examples of the carboxyl protecting group represented by $R^3$ or $R^6$ are protecting groups mentioned in the above-mentioned 'Protective Groups in Organic Synthesis' by Greene, for example straight-chain or branched lower alkyl groups having 1 to 6 carbon atoms such as a methyl group, an ethyl group, a propyl group, an n-butyl group, an isobutyl group, an s-butyl group and a t-butyl group, and an allyl group, a benzyl group, a diphenylmethyl group, and so on, with a methyl group or an ethyl group being preferable for either $R^3$ or $R^6$.

Examples of the amino protecting group represented by $R^4$ or $R^5$ are again protecting groups mentioned in the above-mentioned 'Protective Groups in Organic Synthesis' by Greene, for example a methoxycarbonyl group, a 9-fluorenylmethoxycarbonyl group, a cyclopropylmethoxycarbonyl group, a diisopropylmethoxycarbonyl group, a 2-furanylmethoxycarbonyl group, an isobutoxycarbonyl group, a t-butoxycarbonyl group, a benzyloxycarbonyl group, a formyl group, and so on, with a t-butoxycarbonyl group or a benzyloxycarbonyl group being preferable for either $R^4$ or $R^5$.

Steps of Manufacturing Compound [I] (Substance GM-95) from Compound [II]

(a) Manufacture of Compound [III] from Compound [II]

The present step is a step of deprotecting the macrocyclic compound having general formula [II] by removing the acetal protecting groups (the $R^1$'s) thereof, and forming an oxazole ring through an intramolecular cyclization reaction between the produced formyl group and an amide group.

i) In the above reaction, removing the acetal protecting groups (the $R^1$'s) is carried out in the presence of an acid in a suitable solvent. The solvent may be any solvent so long as it is inert to the reaction; examples are tetrahydrofuran, dioxane, ethyl acetate, and so on. Such solvents may be used alone, or a mixture thereof may be used. Examples of the acid are organic acids such as trifluoroacetic acid and formic acid, and mineral acids such as hydrogen chloride and sulfuric acid. Moreover, the acid can also be used itself. The amount used of the acid is 100 to 2000 mol, preferably 500 to 1000 mol, per mol of the compound having general formula [II]. The reaction temperature is room temperature to about 100° C., preferably about 40° C. to 80° C. The reaction time is about 1 to 48 hours, preferably about 10 to 30 hours.

ii) Next, to form an oxazole ring through an intramolecular cyclization reaction between an amide group and the formyl group produced through the deprotection described above, it is necessary to carry out a dehydration reaction between the formyl group and the amide group in a suitable solvent. The solvent used may be any solvent so long as it is inert to the reaction; examples are chloroform, dichloromethane, ethyl acetate, tetrahydrofuran, dimethylformamide, and soon. Such solvents may be used alone, or a mixture thereof may be used. An example of the dehydrating agent used in the dehydration reaction is a combination of trivalent phosphorous, a halogen and an organic tertiary amine, with a combination of triphenylphosphine, iodine and triethylamine being preferable. Regarding the proportions thereof, 1 to 5 mol of the trivalent phosphorous, 1 to 5 mol of the halogen, and 2 to 10 mol of the organic tertiary amine are used per mol of the compound obtained from deprotecting the compound of general formula [II] by removing the acetal protecting groups. In the specific example, 1 to 5 mol of triphenylphosphine, 1 to 5 mol of iodine, and 2 to 10 mol of triethylamine are used per mol of the compound obtained by deprotecting the compound of general formula [II] by removing the acetal protecting groups.

Regarding the order of addition, it is preferable to add the compound obtained by deprotecting the compound of general formula [II] by removing the acetal protecting groups and then the organic tertiary amine to a mixture of the trivalent phosphorous and the halogen. The reaction temperature is about 0 to 100° C., preferably about 20° C. to 50° C. The reaction time is about 1 to 36 hours, preferably about 12 to 24 hours.

The compound having general formula [III] that is obtained through the present reaction can be used in the next reaction step either after having been isolated or without being isolated. For carrying out isolation, purification can be carried out through ordinary purification methods such as extraction, concentration, crystallization, and column chromatography.

(b) Manufacture of Compound [I] from Compound [III]

The present is a step of deprotecting the macrocyclic compound having general formula [III] by removing the thiol protecting group ($R^2$) thereof, and forming a thiazoline ring through an intramolecular cyclization reaction between the produced thiol group and an amide group.

Using the macrocyclic compound having general formula [III] obtained in (a), reaction is carried out under strongly acidic conditions in a suitable solvent, whereby deprotection through removal of the thiol protecting group ($R^2$) and the intramolecular cyclization reaction proceed simultaneously, and hence substance GM-95 having general formula [I] is produced. The solvent may be any solvent so long as it is one that does not get involved in the reaction; examples are chloroform, dichloromethane, ethyl acetate, tetrahydrofuran, dimethylformamide, and so on, with dichloromethane being preferable. Such solvents may be used alone, or a mixture thereof may be used. Examples of the acid used in setting the strongly acidic conditions are titanium tetrachloride, trifluoroacetic acid/anisole, hydrofluoric acid/anisole, hydrogen chloride/acetic acid, HF, and so on, with titanium tetrachloride being preferable. The amount used of the acid is 1 to 100 mol, preferably 30 to 60 mol, per mol of the compound having general formula [III]. The reaction temperature is about 0 to 100° C., preferably 20° C. to 40° C. The reaction time is 1 to 5 days, preferably 2 to 4 days.

The substance GM-95 having general formula [I] that is obtained through the present reaction can be purified through ordinary purification methods such as extraction, concentration, crystallization, and column chromatography.

Steps of Manufacturing Compound [II] from Compound [IV-a] and Compound [V-a]

(a) Manufacture of Compound [VI] from Compound [IV-a] and Compound [V-a]

The present is a step of carrying out dehydration condensation between an acetal derivative having general formula [IV-a] and a thiol derivative having general formula [V-a] in a suitable solvent.

The solvent used in this intermolecular dehydration condensation reaction may be any solvent so long as it is inert to the reaction; examples are chloroform, dichloromethane, ethyl acetate, tetrahydrofuran, acetonitrile, dimethylformamide, and so on, with dimethylformamide being preferable. Such solvents may be used alone, or a mixture thereof may be used. Examples of the dehydration condensing agent used are dicyclohexylcarbodiimide, a water-soluble carbodiimide, diethylphosphorocyanidate, diphenylphosphoryl azide, triphenylphosphine/diethyl azodicarboxylate, and so on, with a water-soluble carbodiimide being preferable. As a water-soluble carbodiimide, 1-(3-dimethylaminopropyl)-3-ethylcarbodiimide hydrochloride is preferable. In the reaction, the compound having general formula [V-a] can be used in an amount of 0.8 to 1.2 mol, and the dehydration condensing agent in an amount of 1 to 2 mol, preferably 1.0 to 1.3 mol, per mol of the compound having general formula [IV-a]. Furthermore, to promote the reaction and inhibit side reactions, it is preferable to add 1-hydroxybenzotriazole monohydrate, with the proportion used thereof being about 1 to 1.5 mol per mol of the compound having general formula [IV-a]. The reaction temperature is about 0 to 100° C., preferably about 10° C. to 30° C. The reaction time is about 6 to 30 hours, preferably about 8 to 24 hours.

The compound having general formula [VI] that is obtained through the present reaction can be used in the next reaction step either after having been isolated or without being isolated. In the case of carrying out isolation, purification can be carried out through ordinary purification means such as extraction, concentration, crystallization, and column chromatography.

(b) Manufacture of Compound [II] from Compound [VI]

The present is a step of deprotecting the amide derivative having general formula [VI] by removing the carboxyl protecting group and the amino protecting group ($R^3$ and $R^4$), and then carrying out intramolecular cyclization between the amino group and the carboxyl group through intramolecular dehydration condensation.

i) In the above reaction, the deprotection of the amide derivative having general formula [VI] through removal of the carboxyl protecting group ($R^3$) and the amino protecting group ($R^4$) is carried out as follows.

Removing the amino protecting group ($R^4$) from the amide derivative having general formula [VI] is carried out in the presence of an acid in a suitable solvent. The solvent may be any solvent so long as it is inert to the reaction; examples are dichloromethane, methanol, ethanol, tetrahydrofuran, dimethylformamide, and so on, with dichloromethane and methanol being preferable. Such solvents maybe used alone, or a mixture thereof may be used. Examples of the acid used are mineral acids such as hydrogen chloride and sulfuric acid, and organic acids such as trifluoroacetic acid and formic acid, with hydrogen chloride being preferable.

In the present step, it is preferable to select $R^4$ and the $R^1$'s such that $R^4$ is selectively removed leaving the $R^1$'s intact. A preferable combination of $R^4$ and the $R^1$'s is that $R^4$ is a t-butoxycarbonyl group and the $R^1$'s are methyl groups.

The present step is carried out under anhydrous conditions to prevent removal of the $R^1$'s. The amount of the acid is 1 to 10 mol, preferably 4 to 6 mol, per mol of the substrate. The reaction temperature is about 0 to 80° C., preferably about 20 to 50° C. The reaction time is about 1 to 24 hours, preferably about 8 to 18 hours.

Removing the carboxyl protecting group ($R^3$) from the amide derivative having general formula [VI] is carried out in the presence of a base in a suitable solvent. The solvent may be any solvent so long as it is inert to the reaction; examples are methanol, ethanol, tetrahydrofuran, dimethylformamide, and so on, with methanol being preferable. Such solvents may be used alone, or a mixture thereof may be used. Examples of the base used are sodium hydroxide, potassium hydroxide, and so on. The amount of the base is 1 to 10 mol, preferably 2 to 6 mol, per mol of the substrate. The reaction temperature is about 0 to 80° C., preferably about 20 to 50° C. The reaction time is about 1 to 24 hours, preferably about 4 to 18 hours.

It is preferable to select $R^2$ and $R^3$ such that $R^3$ is selectively removed leaving the $R^2$ intact. A preferable combination of $R^2$ and $R^3$ is that $R^2$ is a trityl group and $R^3$ is a methyl group or an ethyl group.

There is no limitation on the order of the acid treatment and base treatment described above, but it is preferable to carry out the acid treatment first and then carry out the base treatment.

ii) After the deprotection described above, the macrocyclic compound having general formula [II] can be obtained through an intramolecular dehydration condensation in a suitable solvent. The solvent may be any solvent so long as it is inert to the reaction; examples are chloroform, dichloromethane, ethyl acetate, tetrahydrofuran, dimethylformamide, and so on, with dimethylformamide being preferable; such solvents may be used alone, or a mixture thereof may be used. Examples of the dehydration condensing agent are dicyclohexylcarbodiimide, a water-soluble carbodiimide, diethyl phosphorocyanidate, diphenylphosphoryl azide, triphenylphosphine/diethyl azodicarboxylate, and so on, with diphenylphosphoryl azide being preferable. At this time, to inhibit intermolecular reaction, it is preferable to carry out the reaction with the concentration of the compound obtained by removing the carboxyl protecting group and the amino protecting group from the compound [VI] at very low concentration. The reaction concentration of the compound obtained from the compound [VI] is 1 to 100 mM, preferably 2 to 20 mM. Moreover, the dehydration condensing agent can be used in an amount of 0.8 to 3 mol, preferably 1 to 2 mol, per mol of the compound obtained from the compound [VI].

To promote the reaction and inhibit side reactions, it is preferable that 1-hydroxybenzotriazole monohydrate, 4-dimethylaminopyridine and triethylamine are present. The proportions used thereof are 1 to 1.5 mol of 1-hydroxybenzotriazole monohydrate, 1 to 1.5 mol of 4-dimethylaminopyridine, and 1 to 2 mol of triethylamine, per mol of the compound obtained by removing the carboxyl protecting group and the amino protecting group from the compound [VI]. The reaction temperature is about 10 to 60° C., preferably about 25° C. to 35° C. The reaction time is about 1 to 6 days, preferably about 2 to 4 days.

The macrocyclic compound having general formula [II] that is obtained through the present reaction can, if necessary, be purified through ordinary purification means such as extraction, concentration, crystallization, and column chromatography.

Steps of Manufacturing Compound [II] from Compound [IV-b] and Compound [V-b]

(a) Manufacture of Compound [VII] from Compound [IV-b] and Compound [V-b]

The present is a step of carrying out dehydration condensation between an acetal derivative having general formula [IV-b] and a thiol derivative having general formula [V-b] in a suitable solvent.

The solvent used in this intermolecular dehydration condensation reaction may be any solvent so long as it is inert to the reaction; examples are chloroform, dichloromethane, ethyl acetate, tetrahydrofuran, acetonitrile, dimethylformamide, and so on, with dimethylformamide being preferable; such solvents maybe used alone, or a mixture thereof may be used. Examples of the dehydration condensing agent used are dicyclohexylcarbodiimide, a water-soluble carbodiimide, diethyl phosphorocyanidate, diphenylphosphoryl azide, triphenylphosphine/diethyl azodicarboxylate, and soon, with a water-soluble carbodiimide being preferable. As a water-soluble carbodiimide, 1-(3-dimethylaminopropyl)-3-ethylcarbodiimide hydrochloride is preferable. In the reaction, the compound having general formula [V-b] can be used in an amount of 0.8 to 1.2 mol, and the dehydration condensing agent in an amount of 1 to 2 mol, preferably 1.0 to 1.3 mol, per mol of the compound having general formula [IV-b]. To promote the reaction and inhibit side reactions, it is preferable to add 1-hydroxybenzotriazole monohydrate, with the proportion used thereof being about 1 to 1.5 mol per mol of the compound having general formula [IV-b]. The reaction temperature is about 0 to 100° C., preferably about 10° C. to 30° C. The reaction time is about 4 to 30 hours, preferably about 8 to 24 hours.

The compound having general formula [VII] that is obtained through the present reaction can be used in the next reaction step either after having been isolated or without being isolated. In the case of carrying out isolation, purification can be carried out through ordinary purification means such as extraction, concentration, crystallization, and column chromatography.

(b) Manufacture of Compound [II] from Compound [VII]

The present is a step of deprotecting the amide derivative having general formula [VII] by removing the amino protecting group and the carboxyl protecting group ($R^5$ and $R^6$), and then carrying out intramolecular cyclization between the amino group and the carboxyl group through intramolecular dehydration condensation.

i) In the above reaction, deprotecting the amide derivative represented by general formula [VII] through removal of the carboxyl protecting group and the amino protecting group ($R^6$ and $R^5$) can be carried out in the same way as the deprotection of the amide derivative having general formula [VI] through removal of the carboxyl protecting group ($R^3$) and the amino protecting group ($R^4$).

Specifically, removing the amino protecting group ($R^5$) from the amide derivative having general formula [VII] is carried out in the presence of an acid in a suitable solvent. The solvent may be any solvent so long as it is inert to the reaction; examples are dichloromethane, methanol, ethanol, tetrahydrofuran, dimethylformamide, and so on, with dichloromethane and methanol being preferable. Such solvents may be used alone, or a mixture thereof may be used. Examples of the acid are mineral acids such as hydrogen chloride and sulfuric acid, and organic acids such as trifluoroacetic acid and formic acid, with hydrogen chloride being preferable.

In the present step, it is preferable to select $R^{15}$ and the $R^1$'s such that $R^5$ is selectively removed leaving the $R^1$'s intact. A preferable combination of $R^5$ and the $R^1$'s is that $R^5$ is a t-butoxycarbonyl group and the $R^1$'s are methyl groups.

The present step is carried out under anhydrous conditions to prevent removal of the $R^1$'s. The amount of the acid is 1 to 10 mol, preferably 4 to 6 mol, per mol of the substrate. The reaction temperature is about 0 to 80° C., preferably about 20 to 50° C. The reaction time is about 1 to 24 hours, preferably about 8 to 18 hours.

Removing the carboxyl protecting group ($R^6$) from the amide derivative having general formula [VII] is carried out in the presence of a base in a suitable solvent. The solvent may be any solvent so long as it does not get involved in the reaction; examples are methanol, ethanol, tetrahydrofuran, dimethylformamide, and so on, with methanol being preferable. Such solvents may be used alone, or a mixture thereof may be used. Examples of the base used are sodium hydroxide, potassium hydroxide, and soon. The amount used of the base is 1 to 10 mol, preferably 2 to 6 mol, per mol of the substrate. The reaction temperature is about 0 to 80° C., preferably about 20 to 50° C. The reaction time is about 1 to 24 hours, preferably about 4 to 20 hours.

In the present step, it is preferable to select $R^2$ and $R^6$ such that $R^6$ is selectively removed leaving $R^2$ intact. A preferable combination of $R^2$ and $R^6$ is that $R^2$ is a trityl group and $R^6$ is a methyl group or an ethyl group.

There is no limitation on the order of the acid treatment and base treatment described above, but it is preferable to carry out the acid treatment first and then carry out the base treatment.

ii) After the deprotection described above, the macrocyclic compound having general formula [II] can be obtained through an intramolecular dehydration condensation reaction in a suitable solvent. For this intramolecular dehydration condensation reaction, the method described earlier (in the manufacture of [II] from [VI]) can be used.

Specifically, the solvent may be any solvent so long as it is inert to the reaction; examples are chloroform, dichloromethane, ethyl acetate, tetrahydrofuran, dimethylformamide, and so on, with dimethylformamide being preferable; such solvents maybe used alone, or a mixture thereof may be used. Examples of the dehydration condensing agent are dicyclohexylcarbodiimide, a water-soluble carbodiimide, diethyl phosphorocyanidate, diphenylphosphoryl azide, triphenylphosphine/diethylazodicarboxylate, and so on, with diphenylphosphoryl azide being preferable. At this time, to inhibit intermolecular reaction, it is preferable to carry out the reaction with the concentration of the compound obtained by removing the carboxyl protecting group and the amino protecting group from the compound [VII] at very low concentration. The reaction concentration of the compound obtained by removing the carboxyl protecting group and the amino protecting group from the compound [VII] is 1 to 100 mM, preferably 2 to 20 mM. Moreover, the dehydration condensing agent can be used in an amount of 0.8 to 3 mol, preferably 1 to 2 mol, per mol of the compound obtained by removing the carboxyl protecting group and the amino protecting group from the compound [VII].

To promote the reaction and inhibit side reactions, it is preferable that 1-hydroxybenzotriazole monohydrate, 4-dimethylaminopyridine and triethylamine are present. The proportions used thereof are 1 to 1.5 mol of 1-hydroxybenzotriazole monohydrate, 1 to 1.5 mol of 4-dimethylaminopyridine, and 1 to 2 mol of triethylamine, per mol of the compound obtained by removing the carboxyl protecting group and the amino protecting group from the compound [VII].

The reaction temperature is about 10 to 60° C., preferably about 25° C. to 35° C. The reaction time is about 1 to 6 days, preferably about 2 to 4 days.

The macrocyclic compound having general formula [II] that is obtained through the present reaction can, if necessary, be purified through ordinary purification means such as extraction, concentration, crystallization, and column chromatography.

Each of the trisoxazole derivatives having general formulae [IV-a], [IV-b], [V-a] and [V-b], which are raw materials, is either a publicly known compound, or else can be synthesized in accordance with methods disclosed in documents such as J. Org. Chem., 58, 1575(1993), J. Org. Chem., 58, 3604 (1993), Tetrahedron Lett., 33, 6267 (1992), Tetrahedron Lett., 35, 2477 (1994), Tetrahedron, 51, 7321 (1995) J. Am. Chem. Soc., 115, 8449 (1993), Tetrahedron Lett., 27, 163(1986), J. Org. Chem., 43, 1624(1978), and Tetrahedron Lett., 38, 331 (1997).

Furthermore, in the present invention, due to asymmetric carbons in the compounds used as the raw materials, optical isomers or diastereomers may exist and in each reaction step; any of these, or a mixture thereof, can be used in the reaction steps in the present invention.

For example, if the configuration of the asymmetric carbon indicated by '*' in compound [V-a] or [V-b] in the scheme of the present invention is R, then the configuration of the asymmetric carbon indicated by '*' in the thiazoline ring in compound [I] will also be R; in turn if the configuration of the asymmetric carbon indicated by '*' in compound [V-a] or [V-b] is S, then the configuration of the asymmetric carbon indicated by '*' in the thiazoline ring in compound [I] will also be S. Moreover, if the configuration of the asymmetric carbon indicated by '*' in compound [V-a] or [V-b] is RS, then the configuration of the asymmetric carbon indicated by '*' in the thiazoline ring in compound [I] will also be RS, and if necessary optical resolution can be carried out.

BEST MODE FOR CARRYING OUT THE INVENTION

Figure 1:
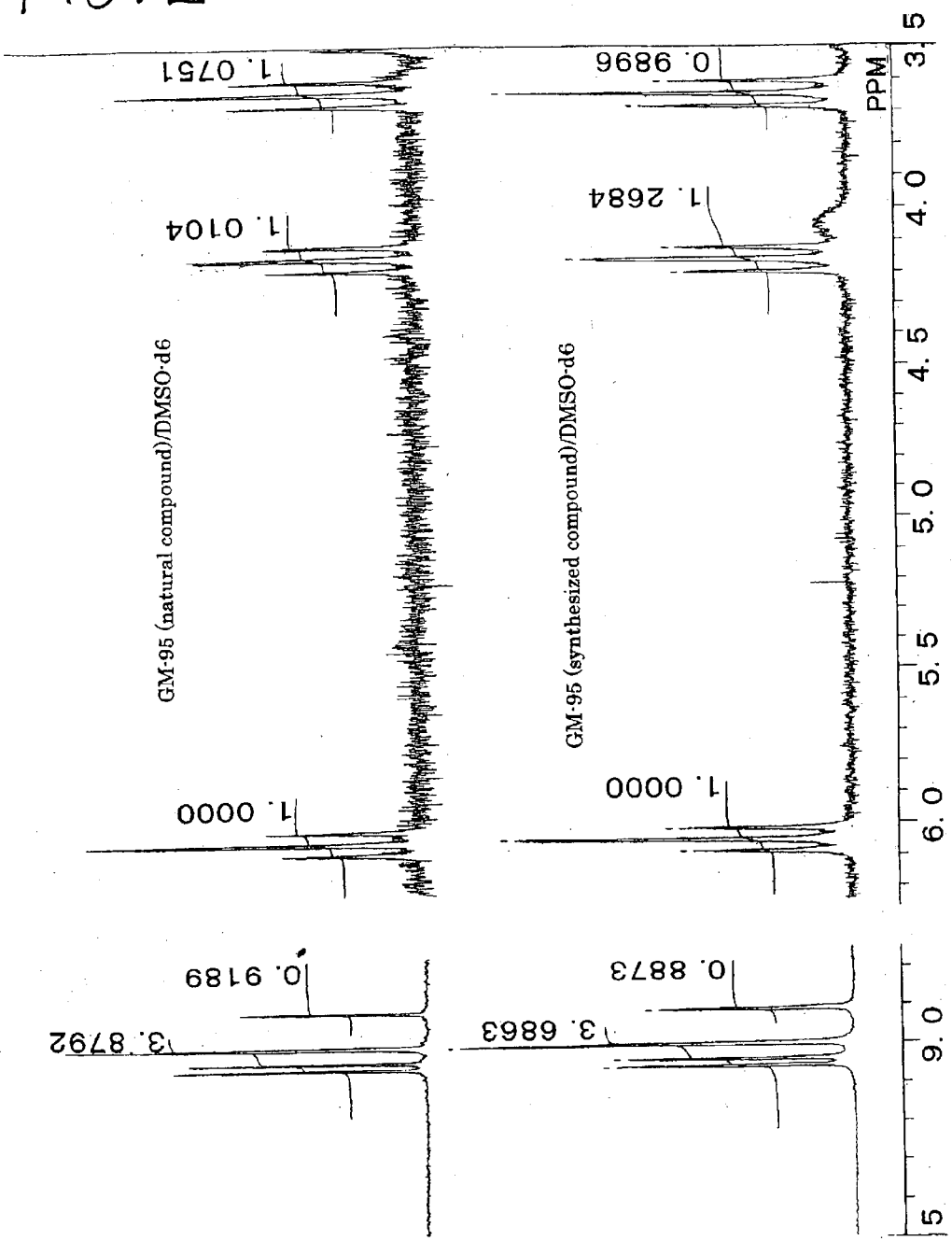
FIG. 1 consists of $^1$H-NMR spectra of GM-95 obtained from a bacterium that produces substance GM-95 disclosed in International Publication No. WO00/24747 as described in Reference Example 3 (natural compound), and GM-95 obtained in Example 6 of the present invention (synthesized compound)

Examples for describing the present invention in more detail are given below; however, the present invention is not limited to these examples.

Following is a more detailed description of the present invention, citing reference examples and examples; however, the scope of the present invention is not limited by these examples.

REFERENCE EXAMPLE 1

Synthesis of methyl 2-{2-[2-(1-amino-2,2-dimethoxyethyl)-1,3-oxazol-4-yl]-1,3-oxazol-4-yl}-1,3-oxazole-4-carboxylate (Compound 1)

([IV-a])

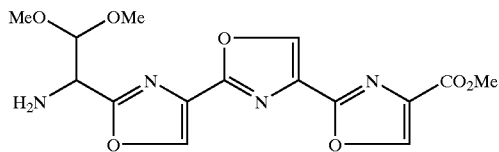

Synthesis was carried out in accordance with methods disclosed in documents such as J. Org. Chem., 58, 1575 (1993), J. Org. Chem., 58, 3604 (1993), Tetrahedron Lett., 33, 6267 (1992), Tetrahedron Lett., 35, 2477 (1994), Tetrahedron, 51, 7321 (1995), J. Am. Chem. Soc., 115, 8449 (1993), Tetrahedron Lett. 27, 163 (1986), J. Org. Chem., 43, 1624 (1978), and Tetrahedron Lett., 38, 331 (1997). 3.90 g (yield: 92.0%) of the stated compound was obtained as a white solid. Physical property values were as follows.

Melting point: 186–188° C.

$^1$H-NMR (CDCl$_3$): δ 8.43 (s, 1H), 8.34 (s, 1H), 8.32 (s, 1H), 4.62 (d, J=5.7 Hz, 1H), 4.29 (d, J=5.7 Hz, 1H), 3.95 (s, 3H), 3.48 (s, 3H), 3.43 (s, 3H), 1.72 (brs, 2H)

Positive ion FAB-MS: m/z=365 [M+H]$^+$

REFERENCE EXAMPLE 2

Synthesis of 2-{2-[2-(1-t-butoxycarbonylamino-2-triphenylmethylthioethyl)-5-methyl-1,3-oxazol-4-yl]-5-methyl-1,3-oxazol-4-yl}-1,3-oxazole-4-carboxylic Acid (Compound 2) ([V-a])

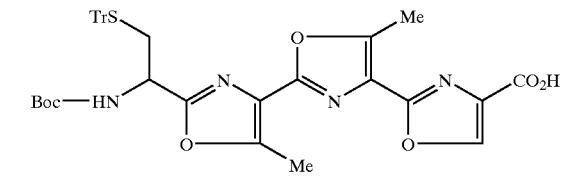

Synthesis was carried out in accordance with methods disclosed in documents such as J. Org. Chem., 58, 1575 (1993), J. Org. Chem., 58, 3604 (1993), Tetrahedron Lett., 33, 6267 (1992), Tetrahedron Lett., 35, 2477 (1994), Tetrahedron, 51, 7321 (1995), J. Am. Chem. Soc., 115, 8449 (1993), Tetrahedron Lett. 27, 163 (1986), J. Org. Chem., 43, 1624 (1978), and Tetrahedron Lett., 38, 331 (1997). The stated compound was obtained. Physical property values were as follows.

$^1$H-NMR (CDCl$_3$): δ 9.45–8.75 (brs, 1H), 8.37 (s, 1H), 7.48–7.15 (m, 15H), 5.43–5.25 (m, 1H), 4.95–4.77 (m, 1H), 2.79 (s, 3H), 2.88–2.60 (m, 2H), 2.68 (s, 3H), 1.43 (s, 9H)

Positive ion FAB-MS: m/z=715 [M+Na]$^+$

EXAMPLE 1

Synthesis of Compound 3

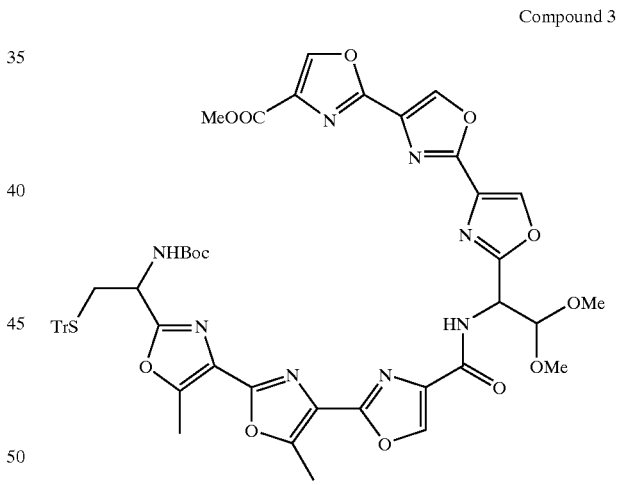

2.5 g (3.5 mmol) of Compound 2 obtained in Reference Example 2 was dissolved in 30 ml of dehydrated dimethylformamide, 590 mg (3.85 mmol) of 1-hydroxybenzotriazole monohydrate, 800 mg (4.17 mmol) of 1-(3-dimethylaminopropyl)-3-ethylcarbodiimide hydrochloride, and then 40 ml of a dehydrated dimethylformamide solution containing 1.34 g (3.68 mmol) of Compound 1 obtained in Reference Example 1 was added while cooling on ice, and then stirring was carried out for 15 hours at room temperature. Solvent was removed from the reaction mixture under reduced pressure, the obtained residue was diluted with ethyl acetate, and the organic layer was washed consecutively with 1N hydrochloric acid, water, saturated sodium hydrogencarbonate aqueous solution, water, and saturated saline solution, and was then dried with anhydrous sodium sulfate. The drying agent was removed by filtration, solvent was removed under reduced pressure, then ether was added to the residue obtained, and the precipitated solid was recovered by filtration. 3.44 g (yield: 94.6%) of the stated compound was obtained as a white solid.

Melting point: 142–143° C.

$^1$H-NMR (CDCl$_3$): δ 8.42 (s, 1H), 8.35 (s, 1H), 8.32 (s, 1H), 8.28 (s, 1H), 7.77 (d, J=8.9 Hz, 1H), 7.43–7.17 (m, 15H), 5.69 (dd, J=8.9, 4.6 Hz, 1H), 5.30–5.10, (m, 1H), 4.90 (d, J=4.6 Hz, 1H), 4.93–4.75 (m, 1H), 3.95 (s, 3H), 3.49, 3.49 (s,s, each 3H), 2.80 (s, 3H), 2.85–2.65 (m, 2H), 2.71 (s, 3H), 1.43 (s, 9H)

Positive ion FAB-MS: m/z=1061 [M+Na]$^+$

EXAMPLE 2

Synthesis of Compound 4

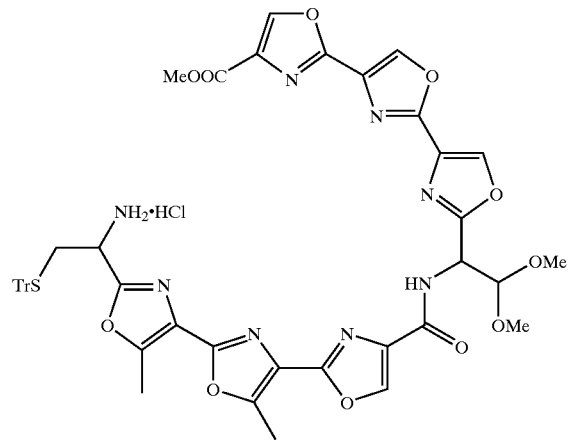

Compound 4

3.33 g (3.2 mmol) of Compound 3 obtained in Example 1 was dissolved in 20 ml of dehydrated dichloromethane and 20 ml of dehydrated methanol, 4.0 ml (16.0 mmol) of a 4N hydrogen chloride-ethyl acetate solution was added while cooling on ice, and stirring was carried out for 14 hours at room temperature and then 2 hours at 35° C. Solvent was removed under reduced pressure, ether was added to the residue obtained, and the precipitated solid was recovered by filtration. 3.01 g (yield: 96.4%) of the stated compound was obtained as a white solid.

Melting point: 163–165° C.

$^1$H-NMR (DMSO-d$_6$): δ 9.09 (s, 1H), 9.03 (s, 1H), 9.01 (s, 1H), 8.84 (s, 1H), 9.15–8.75 (m, 4H), 7.45–7.15 (m, 15H), 5.55–4.37 (m, 1H), 5.11 (d, J=6.6 Hz, 1H), 4.23–4.08, (m, 1H), 3.85 (s, 3H), 3.39, 3.38 (s,s, each 3H), 2.82 (s, 3H), 3.0–2.60 (m, 2H), 2.72 (s, 3H)

Positive ion FAB-MS: m/z=939 [M+H]$^+$

EXAMPLE 3

Synthesis of Compound 5

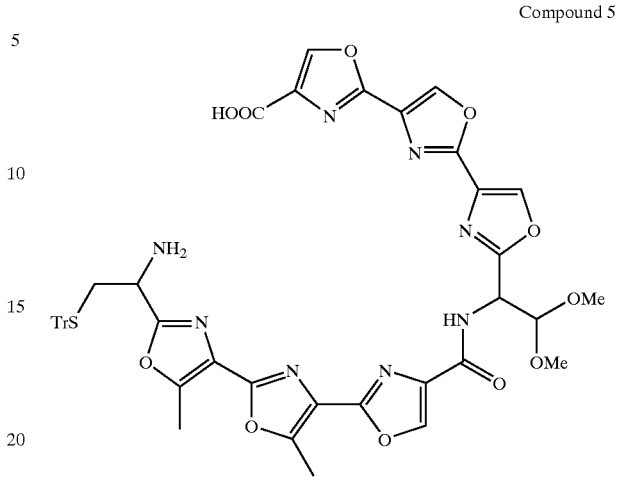

Compound 5

2.93 g (3.0 mmol) of Compound 4 obtained in Example 2 was dissolved in 40 ml of methanol, 9.0 ml (9.0 mmol) of a 1N sodium hydroxide aqueous solution was added while cooling on ice, and stirring was carried for 3 hours at room temperature, then 2 hours at 45° C., and then 1 hour at 60° C. Then, after cooling the reaction mixture to room temperature, solvent was removed under reduced pressure, 50 ml of water and 9.0 ml of 1N hydrochloric acid were added to the obtained residue, and the precipitated solid was recovered by filtration, washed with water and ether, and then dried under reduced pressure. 2.04 g (yield: 73.5%) of the stated compound was obtained as a white solid.

Melting point: 171–174° C.

$^1$H-NMR (DMSO-d$_6$): δ 9.05 (s, 1H), 9.02 (s, 1H), 8.86 (s, 1H), 8.82 (s, 1H), 8.95–8.80 (m, 1H), 7.45–7.15 (m, 15H), 5.47 (dd, J=8.6, 6.9 Hz, 1H), 5.12 (d, J=6.9 Hz, 1H), 3.78–3.65, (m, 1H), 3.39, 3.38 (s,s, each 3H), 2.80 (s, 3H), 2.90–2.50 (m, 2H), 2.66 (s, 3H)

Negative ion FAB-MS: m/z=923 [M−H]$^−$

EXAMPLE 4

Synthesis of Compound 6 ([II])

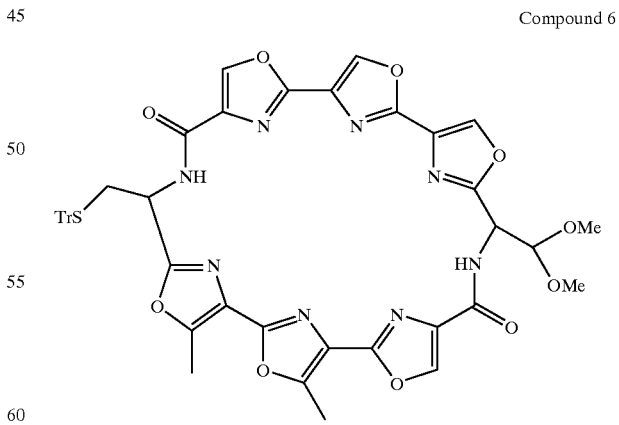

Compound 6

354 mg (2.31 mmol) of 1-hydroxybenzotriazole monohydrate was dissolved in 600 ml of dehydrated dimethylformamide, 10 ml of a dehydrated dimethylformamide solution containing 636 mg (2.31 mmol) of diphenylphosphoryl azide, 308 mg (2.52 mmol) of 4-dimethylaminopyridine, and 10 ml of a dehydrated dimethylformamide solution containing 319 mg (3.15 mmol) of triethylamine were added while cooling on ice, and then 50 ml of a dehydrated dimethylformamide solution containing 1.94 g (2.10 mmol) of Compound 5 obtained in Example 3 also cooled on ice was added dropwise over a period for 15 hours. The obtained reaction mixture (concentration of Compound 5:3.1 mM) was stirred for a further 3 days at room temperature, and then solvent was removed under reduced pressure, and the obtained residue was diluted with chloroform, washed consecutively with 1N hydrochloric acid, water, saturated sodium hydrogencarbonate aqueous solution, water, and saturated saline solution, and then dried with anhydrous sodium sulfate. The drying agent was removed by filtration, solvent was removed under reduced pressure, and the obtained residue was purified using medium pressure silica gel flash column chromatography (methanol:chloroform=1:50 to 1:20) to obtain 1.56 g (yield: 81.9%) of the stated compound as a white solid, this being a mixture of the two diastereomers.

Melting point: 253–256° C. (decomposed)

$^1$H-NMR (DMSO-d$_6$): δ 9.14, 9.13, 9.10, 9.07, 9.02, 8.97, 8.94, 8.91 (s, total 4H), 8.46–8.18 (m, 2H), 7.42–7.13 (m, 15H), 5.60–5.40 (m, 2H), 4.80–4.70 (m, 1H), 3.46, 3.44, 3.36, 3.30 (s, total 6H), 2.77, 2.76, 2.73, 2.71 (s, total 6H), 2.88–2.50 (m, 2H)

Positive ion FAB-MS: m/z=907 [M+H]$^+$

EXAMPLE 5

Synthesis of Compound 7 ([III])

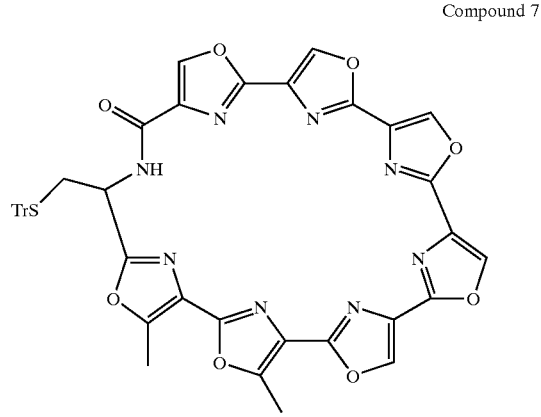

Compound 7

907 mg (1.0 mmol) of Compound 6 obtained in Example 4 was dissolved in 50 ml of formic acid, and stirring was carried out for 20 hours at 50° C. and then 6 hours at 60° C. Then, after cooling the obtained reaction mixture to room temperature, solvent was removed under reduced pressure, saturated sodium hydrogencarbonate aqueous solution and water were added to the obtained residue, and the precipitated solid was recovered by filtration, washed with water and ether, and dried under reduced pressure. 760 mg (yield: 88.3%) of a white solid was obtained. Next, at room temperature, 893 mg (3.52 mmol) of iodine was added to 60 ml of a dehydrated dichloromethane solution containing 923 mg (3.52 mmol) of triphenylphosphine, and stirring was carried out for 15 minutes, and then 70 ml of a dehydrated methylene chloride solution containing the 760 mg (0.88 mmol) of the above-mentioned white solid and 720 mg (7.12 mmol) of triethylamine was added dropwise into the above-mentioned solution, and stirring was carried out for 20 hours at room temperature. The reaction mixture obtained was diluted with chloroform, washed consecutively with 1N hydrochloric acid, water, saturated sodium hydrogencarbonate aqueous solution, water, and saturated saline solution, and then dried with anhydrous sodium sulfate. The drying agent was removed by filtration, solvent was removed under reduced pressure, and the obtained residue was purified using medium pressure silica gel flash column chromatography (methanol:chloroform=1:20 to 1:3). 234 mg (yield: 31.5%) of the stated compound was obtained as a white solid.

Melting point: 246–248° C.

$^1$H-NMR (DMSO-d$_6$): δ 9.11 (S, 1H), 9.05 (s, 1H), 8.98 (s, 1H), 8.96 (s, 1H), 8.96 (s, 1H), 8.32–8.15 (m, 1H), 7.40–7.12 (m, 15H), 5.55–5.42 (m, 1H), 3.05–2.88 (m, 1H), 2.73 (s, 3H), 2.70–2.40 (m, 1H), 2.68 (s, 3H)

Positive ion FAB-MS: m/z=865 [M+Na]$^+$

EXAMPLE 6

Synthesis of Compound 8 (Substance GM-95 [I])

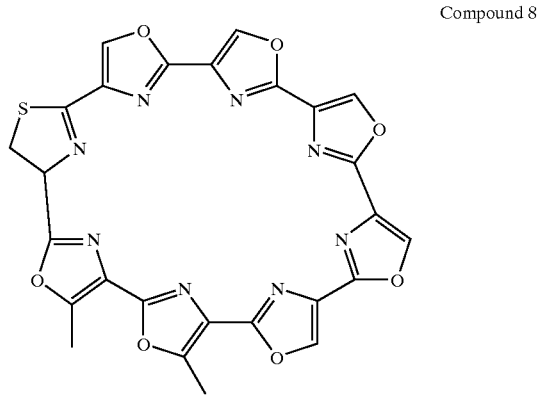

Compound 8

42 mg (0.050 mmol) of Compound 7 obtained in Example 5 was dissolved in 25 ml of dehydrated dichloromethane, 474 mg (2.50 mmol) of titanium tetrachloride was added at room temperature, and stirring was carried out for 3 days at room temperature. Solvent was then removed from the reaction mixture under reduced pressure, and the residue obtained was purified using medium pressure silica gel flash column chromatography (methanol:chloroform=1:10 to 1:4). 10 mg (yield: 34.3%) of the stated compound was obtained as a white solid.

Melting point: 257–260° C. (decomposed)

$^1$H-NMR (DMSO-d$_6$): δ 9.05 (S, 1H), 9.04 (s, 1H), 9.00 (s, 2H), 8.91 (s, 1H), 6.11–5.98 (m, 1H), 4.23–4.10 (m, 1H), 3.72–3.58 (m, 1H), 2.74 (s, 3H), 2.69 (s, 3H)

Positive ion FAB-MS: m/z=605 [M+Na]$^+$

REFERENCE EXAMPLE 3

Determination of Structure of Compound 8

(1) Isolation and Purification of Substance GM-95 Crystals

About 100 g of a methanol extract containing substance GM-95 obtained from the bacterium by culturing under the similar culture conditions as disclosed in International Publication No. WO00/24747 was loaded onto the silica gel column chromatography (60 mm inside diameter×500 mm) and eluted using methanol and methylene chloride (ratio 1:9) as mobile phase at a flow rate of 40 ml/min. The fraction containing the substance GM-95 was detected using the method disclosed in International Publication No. WO00/24747. The fraction concentration residue obtained by carrying out this operation four times was treated with ethyl acetate, whereby 759 mg of insoluble matter was obtained. The insoluble matter obtained was loaded onto the silica gel column chromatography (50 mm inside diameter×500 mm) and eluted using methanol and methylene chloride (ratio 1:9 to 1:5) as mobile phase at a flow rate of 40 ml/min. The fraction of substance GM-95 was collected under the above detection conditions and concentrated, and the obtained residue obtained was treated with ethyl acetate. 117 mg of powdery substance GM-95 crystals was obtained. With the exception of the melting point, the physico-chemical properties of the obtained substance GM-95 crystals and that of the GM-95 residue obtained by evaporation disclosed in International Publication No. WO00/24747 are identical. The melting point of the obtained substance GM-95 crystals under the present purification conditions was above 235° C. (decomposed).

The substance GM-95 crystals obtained through the purification described above were taken as a reference, and used in the identification of Compound 8 obtained according to the present invention.

(2) Determination of Structure of Compound 8

Figure 2:
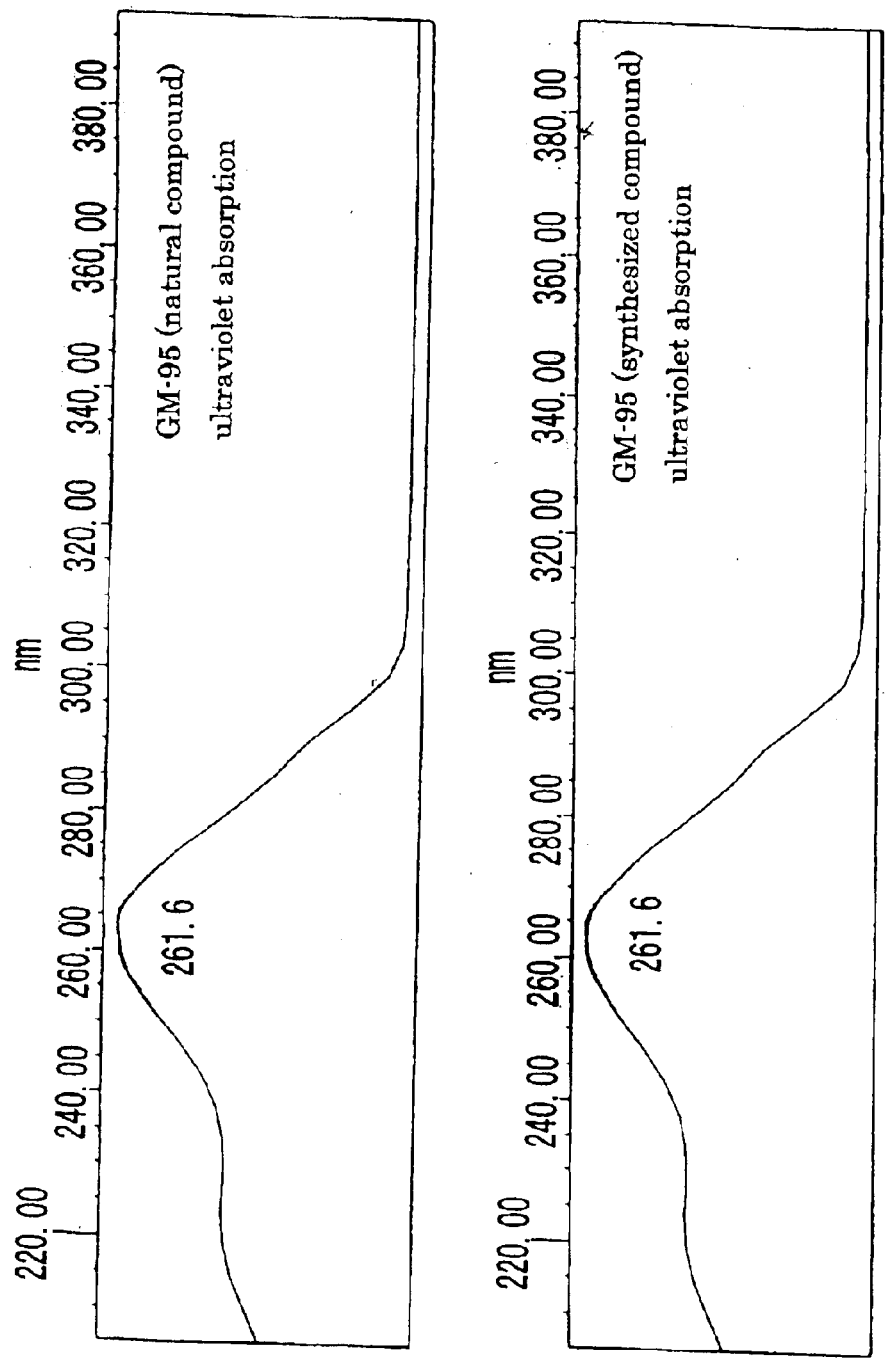
FIG. 2 consists of ultraviolet absorption spectra of the GM-95 obtained from the bacterium that produces substance GM-95 disclosed in International Publication No. WO00/24747 as described in Reference Example 3 (natural compound), and the GM-95 obtained in Example 6 of the present invention (synthesized compound)
Figure 3:
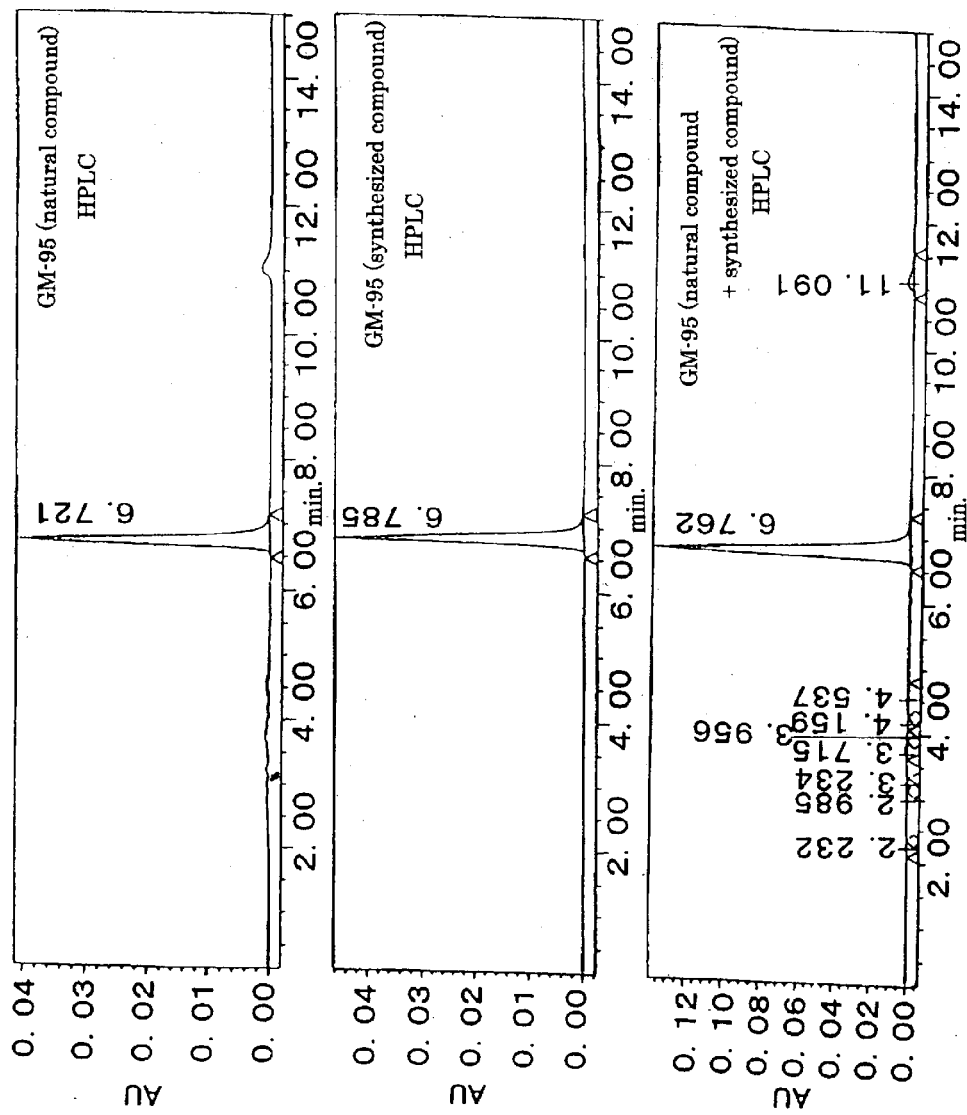
FIG. 3 consists of HPLC spectra of the GM-95 obtained from the bacterium that produces substance GM-95 disclosed in International Publication No. WO00/24747 as described in Reference Example 3 (natural compound), and the GM-95 obtained in Example 6 of the present invention (synthesized compound).

The $^1$H-NMR (DMSO-$d_6$) spectra of Compound 8 obtained in Example 6 and the substance GM-95 crystals obtained in (1) above were compared (see FIG. 1). Furthermore, comparisons of the retention times (Rt) for high performance liquid chromatography (HPLC) and the UV spectra were carried out (see FIG. 2 and FIG. 3). The HPLC analysis conditions were set according to the methods disclosed in International Publication No. WO00/24747. That is, measurement was carried out under the following conditions:

Column: Pegasil ODS (4.6 mm (inside diameter)×250 mm; made by Senshu Scientific Co., Ltd.)

Mobile phase: Acetonitrile/trifluoroacetic acid/water (70:0.1:30 v/v/v)
Flow rate: 1 ml/min
Detection: 254 nm From the results (the ultraviolet absorption spectra conformity, the NMR spectra conformity, and the HPLC retention times conformity) and also the mass spectroscopy result shown in Example 6, it was ascertained the Compound 8 has an identical structure to substance GM-95.

INDUSTRIAL APPLICABILITY

According to the present invention, substance GM-95, which has an anti-cancer activity, can be synthesized chemically.

Moreover, the compounds having general formulae [II] and [III] are useful as manufacturing intermediates for chemically synthesizing substance GM-95, which has an anti-cancer activity.

What is claimed is:

1. A method of manufacturing substance GM-95 having general formula [I]

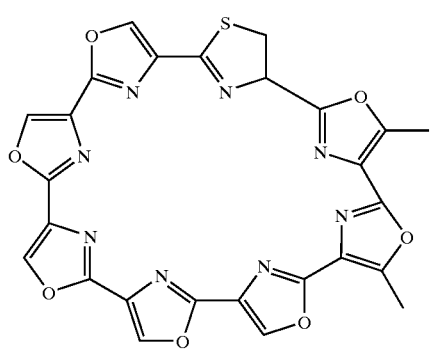

[I]

comprising deprotecting the thiol protecting group ($R^2$) of a macrocyclic compound represented by general formula [III]

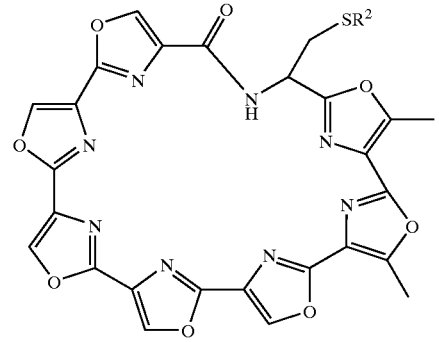

[III]

(wherein, $R^2$ represents a thiol protecting group) and forming a thiazoline ring through an intramolecular cyclization reaction between the produced thiol group and an amide group.

2. A method of manufacturing substance GM-95 having general formula [I]

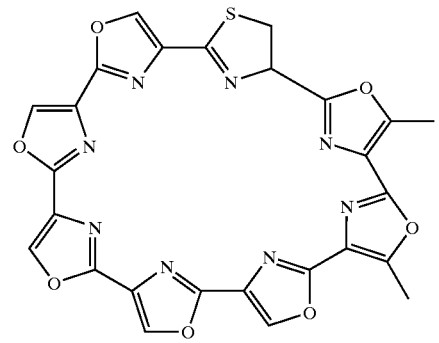

[I]

comprising (a) deprotecting acetal protecting groups (the $R^1$'s) of a macrocyclic compound represented by general formula [II]

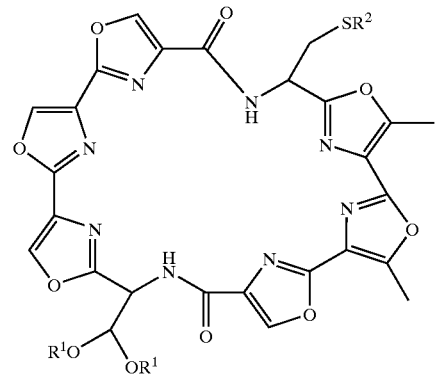

[II]

(wherein, $R^1$'s are the same or different and each represents a lower alkyl group, and $R^2$ represents a thiol protecting group) and forming an oxazole ring through an intramolecular cyclization reaction between the said produced formyl group and an amide group, and (b) deprotecting the thiol protecting group ($R^2$) of the said obtained macrocyclic compound represented by general formula [III]

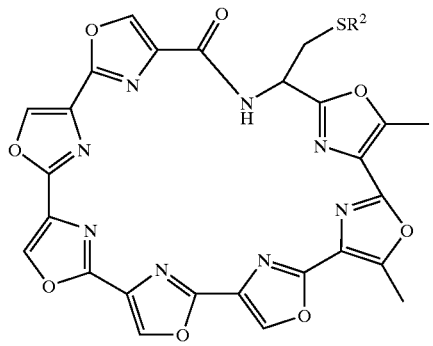

[III]

(wherein, $R^2$ is as mentioned above) and forming a thiazoline ring through an intramolecular cyclization reaction between the said thiol group and an amide group.

3. A macrocyclic compound having general formula [III]

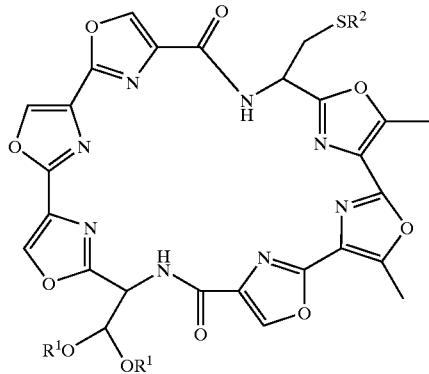

[II]

(wherein, the $R^1$'s and $R^2$ are as mentioned above).

4. A macrocyclic compound having general formula [III]

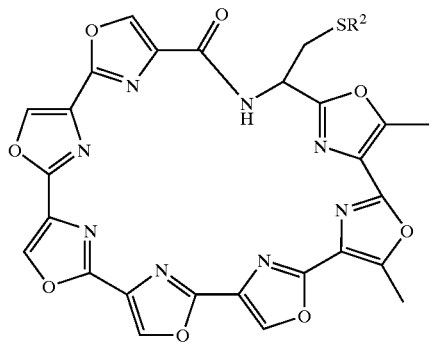

[III]

(wherein, $R^2$ is as mentioned above).

5. A method of manufacturing a macrocyclic compound having general formula [II]

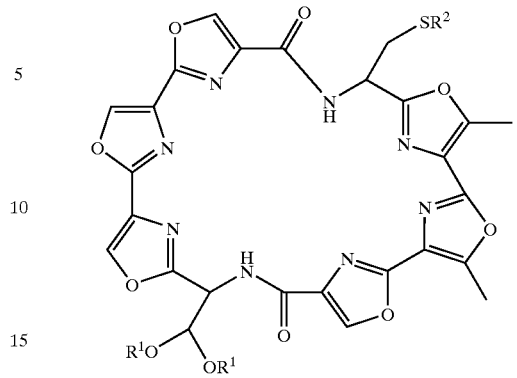

[II]

(wherein, the $R^1$'s and $R^2$ are as mentioned above) comprising (a) carrying out dehydration condensation between an acetal derivative represented by general formula [IV-a]

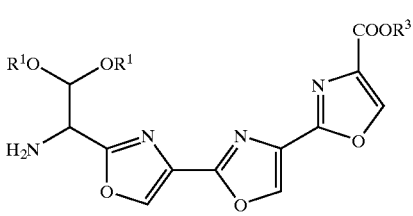

[IV-a]

(wherein, the $R^1$'s are as mentioned above, and $R^3$ represents a carboxyl protecting group) and a thiol derivative having general formula [V-a]

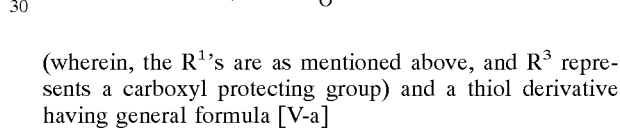

[V-a]

(wherein, $R^2$ is as mentioned above, and $R^4$ represents an amino protecting group), and (b) deprotecting the amino protecting group ($R^4$) and the carboxyl protecting group ($R^3$) of a thus obtained amide derivative represented by general formula [VI]

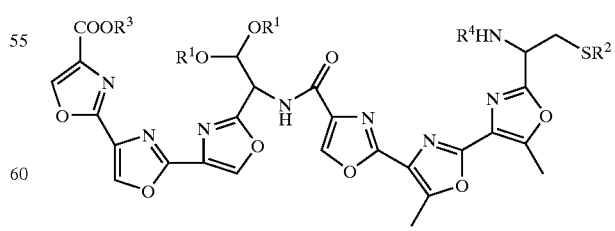

[VI]

(wherein, the $R^1$'s, $R^2$, $R^3$ and $R^4$ are as mentioned above) and then carrying out intramolecular cyclization.

6. A method of manufacturing a macrocyclic compound having general formula [II]

[II]

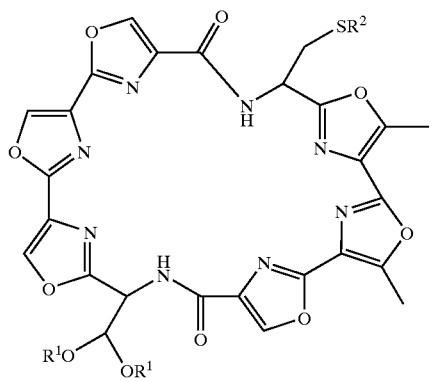

(wherein, the $R^1$'s and $R^2$ are as mentioned above) comprising (a) carrying out dehydration condensation between an acetal derivative having general formula [IV-b]

[IV-b]

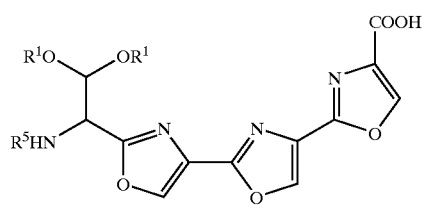

(wherein, the $R^1$'s are as mentioned above, and $R^5$ represents an amino protecting group) and a thiol derivative having general formula [V-b]

[V-b]

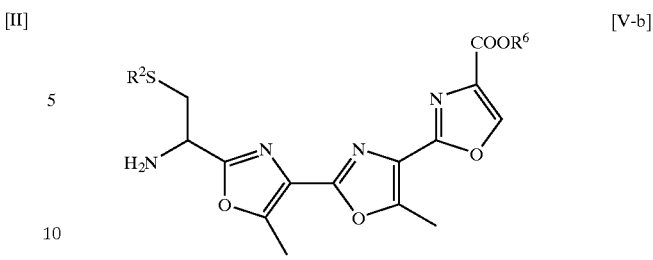

(wherein, $R^2$ is as mentioned above, and $R^6$ represents a carboxyl protecting group), and (b) deprotecting the amino protecting group ($R^5$) and the carboxyl protecting group ($R^6$) of a thus obtained amide derivative represented by general formula [VII]

[VII]

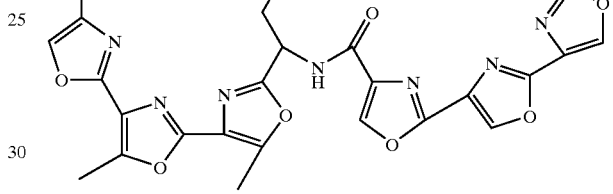

(wherein, the $R^1$'s, $R^2$, $R^5$ and $R^6$ are as mentioned above) and then carrying out intramolecular cyclization.

* * * * *

UNITED STATES PATENT AND TRADEMARK OFFICE
CERTIFICATE OF CORRECTION

PATENT NO.   : 6,818,764 B2
DATED        : November 16, 2004
INVENTOR(S)  : Shozo Yamada et al.

It is certified that error appears in the above-identified patent and that said Letters Patent is hereby corrected as shown below:

Title page,
Item [54], Title, should read -- METHOD OF MANUFACTURING SUBSTANCE GM-95 --

Signed and Sealed this

Twenty-fourth Day of May, 2005

JON W. DUDAS
*Director of the United States Patent and Trademark Office*